(12) United States Patent
Mathieu et al.

(10) Patent No.: US 7,442,208 B2
(45) Date of Patent: Oct. 28, 2008

(54) INTERSPINAL PROSTHESIS

(75) Inventors: Claude Mathieu, Bettlach (CH); Beat Lechmann, Bettlach (CH); Paul Pavlov, Nijmwegen (NL)

(73) Assignee: Synthes (U.S.A.), West Chester, PA (US)

( * ) Notice: Subject to any disclaimer, the term of this patent is extended or adjusted under 35 U.S.C. 154(b) by 393 days.

(21) Appl. No.: 10/784,046

(22) Filed: Feb. 20, 2004

(65) Prior Publication Data
US 2004/0199255 A1 Oct. 7, 2004

Related U.S. Application Data

(63) Continuation of application No. PCT/CH01/00509, filed on Aug. 20, 2001.

(51) Int. Cl.
*A61F 2/44* (2006.01)
(52) U.S. Cl. .............................. 623/17.11; 623/17.16
(58) Field of Classification Search ............. 623/17.13, 623/17.14, 17.15, 21.15, 17.11, 17.16; 606/61; 285/145.1, 358
See application file for complete search history.

(56) References Cited

U.S. PATENT DOCUMENTS

| | | | | |
|---|---|---|---|---|
| 4,932,975 A | | 6/1990 | Main et al. ............... | 623/17.12 |
| 5,261,908 A | * | 11/1993 | Campbell, Jr. ............... | 606/61 |
| 5,491,882 A | * | 2/1996 | Walston et al. ............. | 29/419.1 |
| 5,496,318 A | | 3/1996 | Howland et al. ............... | 606/61 |
| 5,836,948 A | | 11/1998 | Zucherman et al. | |
| 5,888,224 A | | 3/1999 | Beckers et al. | |
| 6,174,334 B1 | * | 1/2001 | Suddaby .................. | 623/17.11 |
| 6,440,169 B1 | | 8/2002 | Elberg et al. | |
| 6,524,341 B2 | * | 2/2003 | Lang et al. ............... | 623/17.15 |
| 6,626,944 B1 | | 9/2003 | Taylor | |
| 6,660,038 B2 | * | 12/2003 | Boyer et al. ............. | 623/17.15 |

FOREIGN PATENT DOCUMENTS

| | | |
|---|---|---|
| FR | 2774581 | 8/1999 |
| WO | WO 9508306 | 3/1995 |
| WO | WO 9531158 A1 * | 11/1995 |

* cited by examiner

*Primary Examiner*—Brian E. Pellegrino
(74) *Attorney, Agent, or Firm*—Stroock & Stroock & Lavan

(57) ABSTRACT

A prosthesis for use in maintaining an interspinal space is disclosed. The prosthesis may be provided as first and second substantially symmetrical halves. The first and second halves may each have a coupling portion and a process portion. The coupling portions allow the separate halves to be separately fit within the interspinal space and then connected to form a single prosthesis, eliminating the need for cutting connecting ligaments to allow insertion of the prosthesis. Various connection and locking arrangements are disclosed to maintain the halves engaged with each other and the interspinal space.

10 Claims, 5 Drawing Sheets

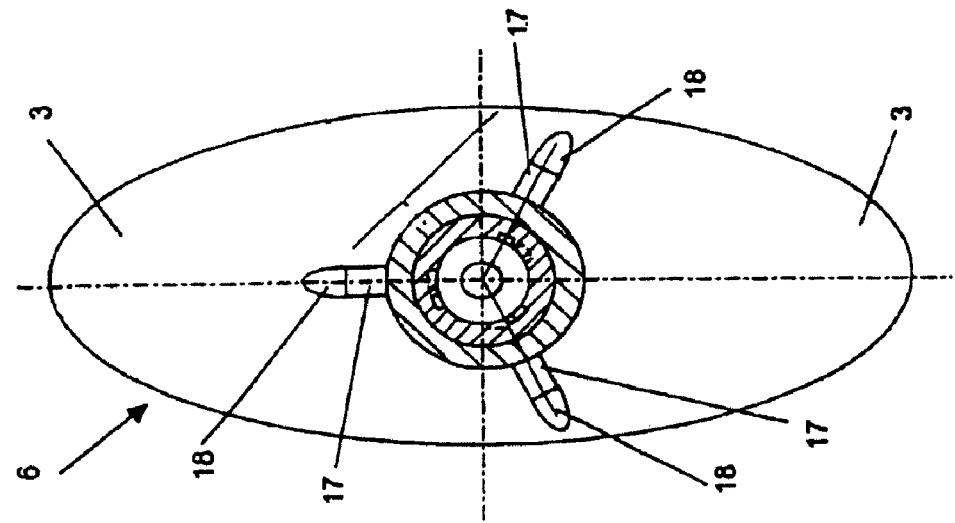
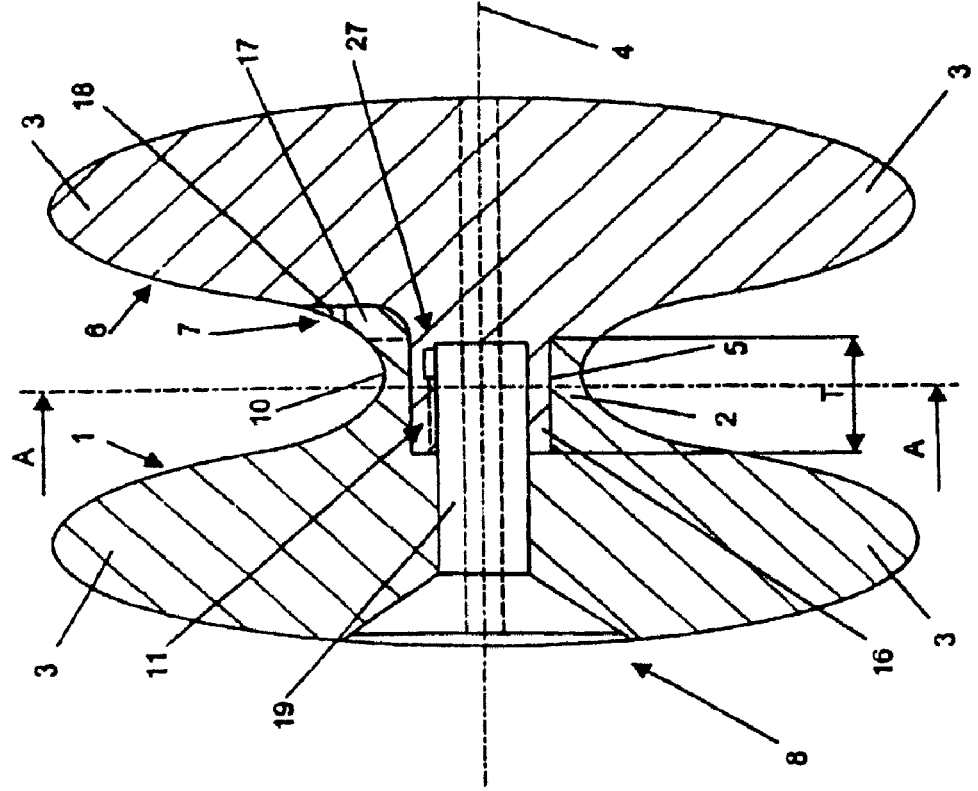
Fig. 1a
Fig. 1b

INTERSPINAL PROSTHESIS

CROSS-REFERENCE TO EARLIER-FILED APPLICATION

This application is a continuation of co-pending PCT application serial number PCT/CH01/00509, filed Aug. 20, 2001, the entirety of which application is incorporated herein by reference thereto.

BACKGROUND OF THE INVENTION

The invention relates to an interspinal prosthesis with a central part having a central axis, which can be introduced into the interspinal space, an inner end and an outer end, as well as two processes, which arise at the outer end, the two processes extending radially and diametrically with respect to the central axis and which can be introduced into the space between the spinal processes of two adjacent vertebrae, a counterpart thereto as well as to a multi-part interspinal prosthesis combined therefrom.

Such prostheses function as spacers for two adjacent vertebrae in the case of a defective disk, which would otherwise reduce the distance between the vertebrae. The stress on the facet joints is also relieved by the enlarged distance.

W099/42051 discloses an interspinal prosthesis of this type, which includes a central piece, which is to be introduced into the interspinal space and from which a pair of ears arises cranially and caudally to the right and to the left of the central piece, in order to hold the central piece in the space between the spinous processes (processus spinosus) of two adjacent vertebrae after an implantation. A disadvantage of this known prosthesis is the fact that the latter is in one piece, which makes the implantation more difficult, so that it is necessary to remove the supraspinal ligament. The removal of this ligament has the disadvantage that the prosthesis is not held securely in the dorsal direction. For this reason, it is proposed in W099/42051 that the prosthesis be drilled through in the interspinal central piece, in order to pass a tape through the borehole, with which tape the prosthesis can be tied to the spinous processes of the adjacent vertebrae. This procedure is very time-consuming and complicated.

The above discussion of the state of the art is given only to explain the environment of the invention and does not mean that the cited state of the art was also actually published or publicly known at the time of this application or its priority.

SUMMARY OF THE INVENTION

The invention is to provide a remedy here. It is therefore an object of the invention to provide an interspinal prosthesis, which can be implanted while the supraspinal ligament is retained, so that the operation, as a whole, can be carried out more gently and the implant secured dorsally without additional means.

Pursuant to the invention, this objective is accomplished with a multi-part, interspinal prosthesis, the individual parts of which may have different mechanical properties.

The inventive, interspinal prosthesis includes essentially a central piece with a central axis, which can be introduced into the interspinal space, and two processes, which arise at the outer ends and extend radially and diametrically to the central axis and can be introduced into the space between the spinous processes of two adjacent vertebrae. Furthermore, at the inner end of the central piece, averted from the spinous processes, there is an axial depression, which accommodates an essentially symmetrical counterpart to the prosthesis.

In a preferred embodiment, the central piece has coupling means, with which the counterpart can be fixed to the prosthesis. The coupling means therefore are constituted so that the positions of the processes at the prosthesis and the positions of the processes at the counterpart are determined relative to one another when the counterpart is fixed in position. Preferably, the coupling means consist of a slide lock, which has a stop, so that, when the counterpart is attached to the prosthesis, the processes assume their desired positions at the prosthesis and the counterpart. Instead, of with a slide lock, the two parts can also be fixed to one another by a screwed or conical connection. In this case, the prosthesis and the counterpart preferably have a twisting safeguard, so that the counterpart can be introduced only in a particular position into the axial depression at the prosthesis. A different configuration of the coupling means consist of at least one elastically deformable cam, which, after the prosthesis and counterpart are assembled, can be locked or snapped into position in the latter.

In a different, preferred embodiment of the inventive prosthesis, the coupling means comprise at least one elastically deformable cam, which, when the prosthesis and counterpart are being assembled, can be deformed elastically and, after the prosthesis and counterpart are assembled, can be locked in position in a complementary depression.

A preferred further development consist therein that the cross-sectional planes, orthogonal to the central axis:
a) have an area of 50 to 300 mm$^2$ and preferably of 70 to two 250 mm$^2$ through the central piece at its narrowest site in the area of the inner end and
b) an area of 70 to 500 mm$^2$ and preferably of 100 to 450 mm$^2$ through the processes.

Furthermore, the prosthesis is produced preferably from an elastic material, so that the central piece can be elastically deformed radially. Preferably the central portion of the prosthesis is capable of deforming from about 10% to about 50%, more preferably from about 15% to about 50% relative to its unstressed diameter. A sufficient radial, elastic deformability can be achieved by producing the prosthesis from a plastic or by producing the central piece with cogs, which can be deformed radially and elastically.

The prosthesis may also be produced from an elastomer, silicone or a polymer from the polycarbonate family. It is, however, also possible to produce a prosthesis from a metallic material, if the elasticity of the prosthesis in the region of the central piece, which comes to rest in the interspinal space, can be realized by means of suitable mechanical devices.

In a different embodiment of the inventive prosthesis, the latter is constructed hollow, the hollow walls being collapsible and/or expandable by filling up the hollow spaces. The collapsible hollow walls have the advantage that, as a result, greater deformation of the prosthesis is made possible than would be permitted by an elastic material.

In the region of the inner end, the outer surface of the central piece can be smooth or roughened. The adhesion of the bone to the prosthesis can be affected by the configuration of the outer surface, being promoted by a rough outer surface and made more difficult or even prevented by a smooth outer surface. The surface of the implant, which is in contact with the bone, can also be protected by embedding hydroxy apatite (HA).

In a preferred embodiment, the inventive counterpart comprises an inner end, an outer end as well as two processes, which arise at the outer end, also extend radially and diametrically and can be inserted in the space opposite the prosthesis and between the spinous processes of two adjacent vertebras. Moreover, a peg, directed toward the inner end, is mounted at the counter part and can be introduced into the depression at the prosthesis. With that, an exact alignment of the prosthesis and the counterpart can be attained during the implantation.

Like the prosthesis, the counterpart can be fitted out with analogous, respectively complementary coupling means. Once again, these coupling means may comprise a slide lock, elastically deformable cams or a screwed or a conical connection. Likewise, an analogous, respectively complementary twisting safeguard is mounted at the counterpart.

The preferred embodiment of the inventive, interspinal prosthesis with a counterpart is distinguished owing to the fact, in the assembled state, it has a plane of symmetry orthogonal to the central axis, the processes of the interspinal prosthesis being at a distance of at least 2 mm and preferably of at least 3 mm from those of the counterpart, when viewed parallel to the central axis. The maximum distance of the processes of the interspinal prosthesis from those of the counterpart is 15 mm and preferably 12 mm.

The invention and further developments of the invention are explained in even greater detail in the following by means of partially diagrammatical representations of several examples. In the drawings,

BRIEF DESCRIPTION OF THE DRAWINGS

FIG. 1a shows a section through the preferred embodiment of the inventive, interspinal prosthesis with counterpart, FIG. 1b shows a side view of the preferred embodiment of the embodiment of the inventive prosthesis with counterpart, shown in FIG. 1a, FIG. 2 shows a section through a different embodiment of the inventive interspinal prosthesis with a counterpart.

DETAILED DESCRIPTION OF THE INVENTION

Figure 2:
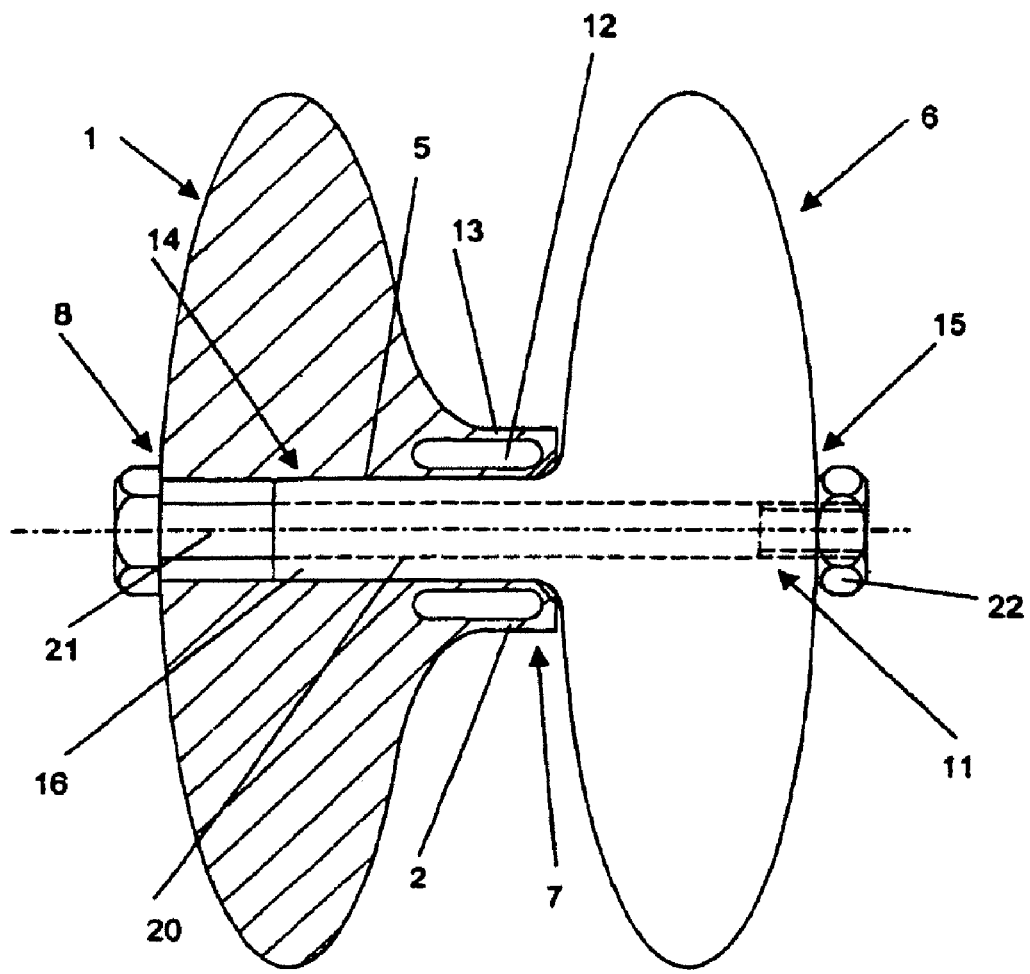

In FIG. 1, the interspinal prosthesis 1 with the counterpart 6 is shown in the assembled state. The central piece 2 of the prosthesis 1, with the inner end 7 of the prosthesis 1, adjoins the counterpart 6. At the outer end 8 of the prosthesis 1, the two processes 3 are disposed perpendicularly to the central axis 4 and diametrically opposite to one another. In the embodiment shown here, the processes 3 are constructed as halves of an ellipsoid body. The also radial and diametrically opposite to one another processes 3 of the counterpart 6 are disposed symmetrically to a plane, which is orthogonal to the central axis 4. Three radial cams 17, which are disposed symmetrically when viewed in the cross-section of the prosthesis 1 parallel to the central axis 4, protrude at the central piece 2 at the inner end 7 of the prosthesis and engage complementary grooves 18 at the counterpart 6, function as twisting safeguard between the prosthesis 1 and the counterpart 6. Coaxially with the central axis 4, the central part 2 includes a depression 5, which penetrates from the inner end 7 into the prosthesis 1 up to a depth T. The counterpart 6 has a peg 16, which is constructed to be complementary to the depression 5 and accordingly, during the assembly of the prosthesis 1 and the counterpart 6, can be introduced into the depression 5. Furthermore, the prosthesis 1 comprises a fixing-in-position bolt 19 with a bolt head 26, which can be brought into contact with the outer end 8 of the prosthesis 1. The fixing-in-position bolt can be passed coaxially with the central axis 4 through the prosthesis 1 and locked by means of a slide lock 27 in the peg 16 of the counterpart 6, so that the prosthesis 1 can be locked detachably with the counterpart 6. A borehole 20, coaxial with the central axis 4, passes through the fixing-in-position bolt 19 and the counterpart 6, so that the prosthesis 1 and the counterpart 6 can be collapsed radially.

FIG. 2 shows a further embodiment of the prosthesis with the counterpart 6 in the assembled state. The depression 5 passes through the prosthesis 1 coaxially from the inner end 7 up to the outer end 8. During the assembly of the prosthesis 1 and the counterpart 6, the peg 16 at the counterpart 6 is pushed into the through depression until the inner end 7 of the prosthesis 1 comes up against the processes 3 of the counterpart 6. Moreover, a borehole 20 is drilled through the counterpart 6 between the outer end 15 and the inner end 14. The coupling means 11 are constructed as a screwed connection, the screw 21 being passed through the depression 5 at the prosthesis 1 and through the borehole 20 at the counterpart 6 from the outer end 8 of the prosthesis 1 up to the outer end 15 of the counterpart 6 and bolted with a nut 22. In addition, the prosthesis 1 is provided with a hollow space 12, so that the walls 13 of the hollow space can be collapsed or, by filling the hollow space 12 with a filling material, expanded.

Figure 3:
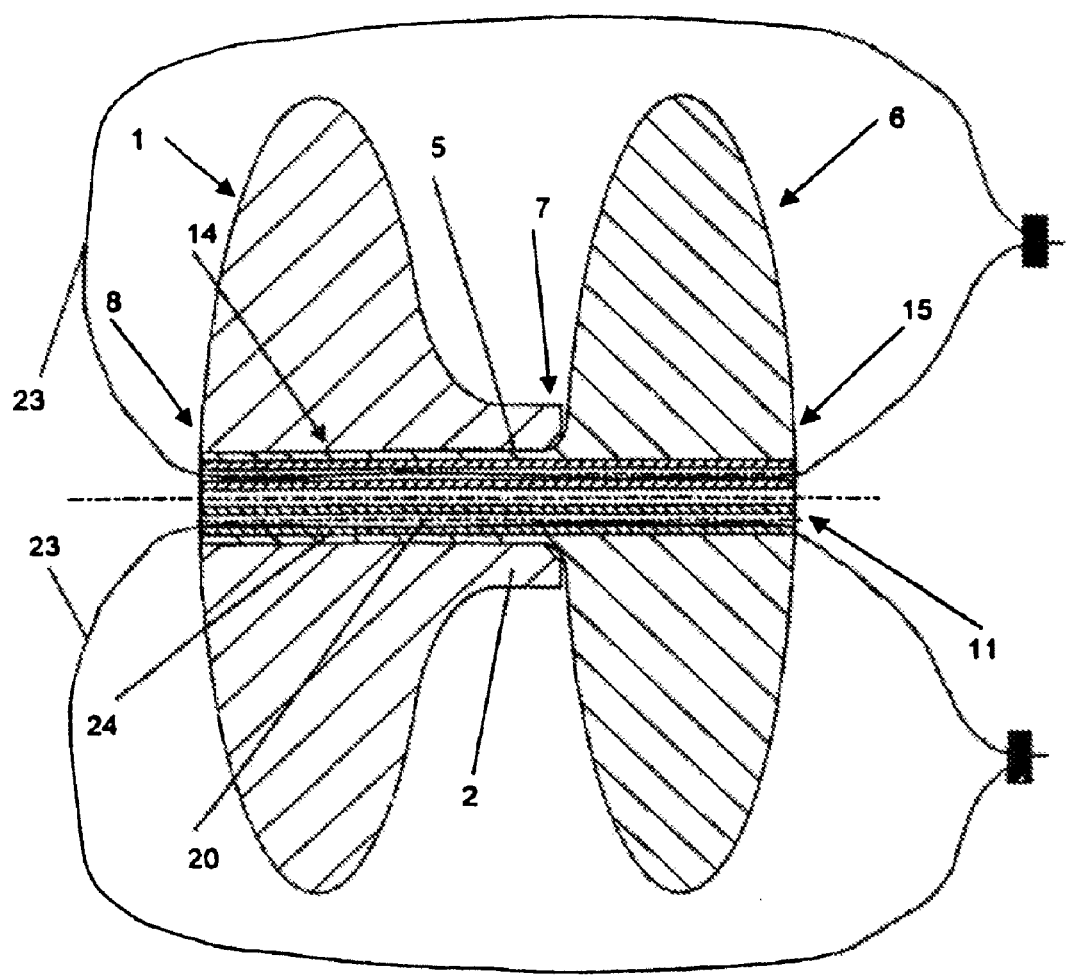
FIG. 3 shows a section once again through a different embodiment of the inventive interspinal prosthesis with a counterpart.

The embodiment, shown in FIG. 3, differs from the embodiments described above in that the peg 16 at the counterpart 6 is passed completely through the depression 5 at the prosthesis 1, so that the inner end 14 of the counterpart 6 aligns with the outer end 8 of the prosthesis 1 furthermore, the counterpart 6 has several boreholes 20, which are continuous from the inner end 14 to the outer end 15 and the axes of which extend parallel to the central axis 4. The cerclage wires 23, by means of which the interspinal prosthesis 1 and the counterpart 6 are fixed in position, can be passed through these boreholes 21.

Figure 4:
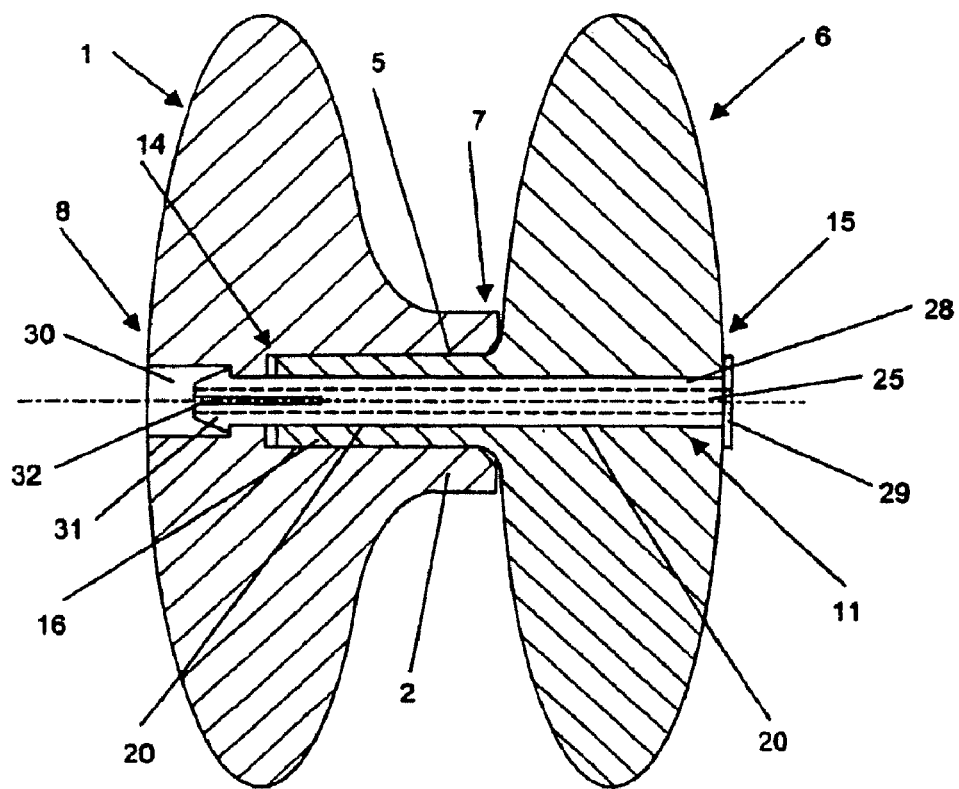
FIG. 4 shows a section through a further embodiment of the inventive interspinal prosthesis with a counterpart and FIG. 5 shows a view of a further embodiment of the inventive interspinal prosthesis with a counterpart.
Figure 5:
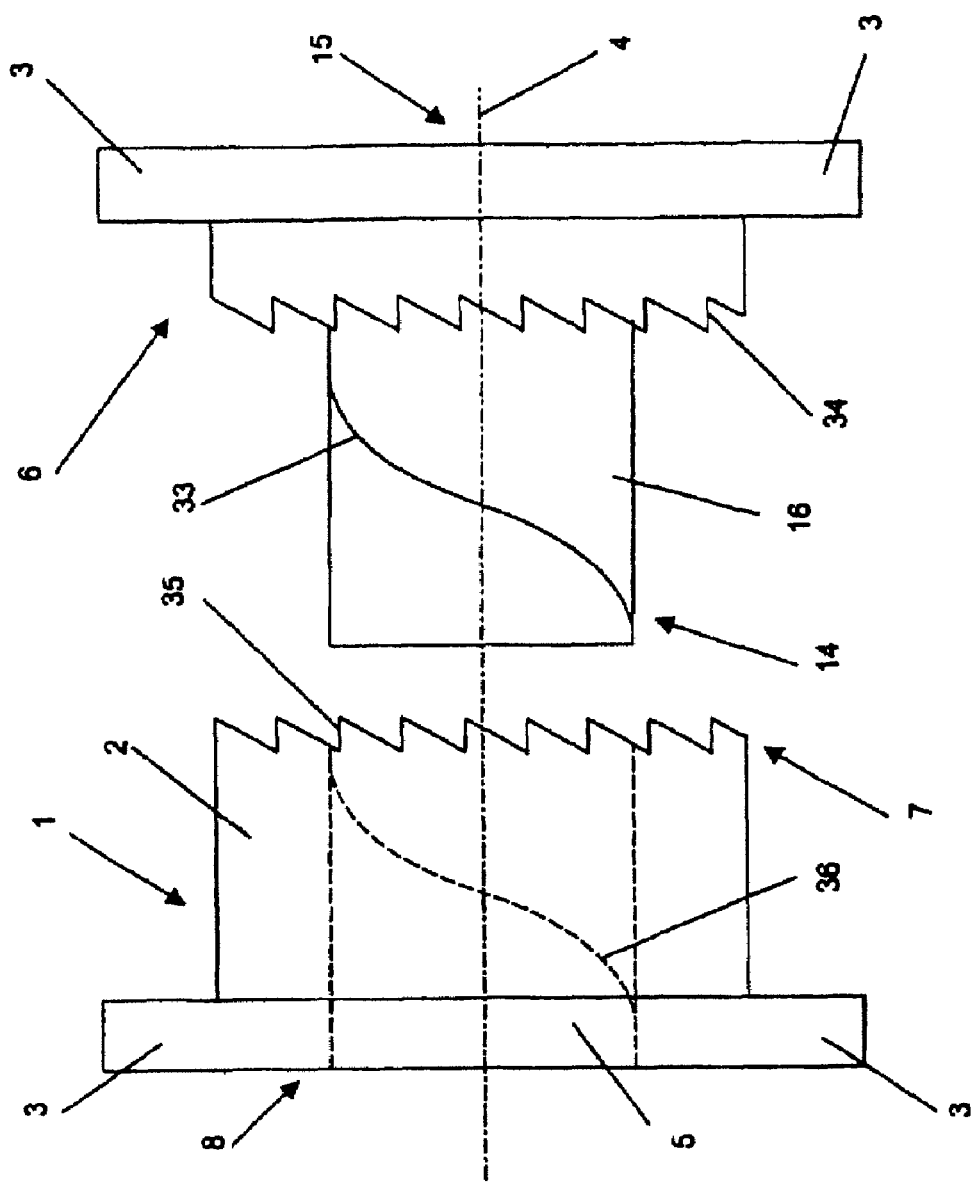

The embodiment, shown in FIG. 4, differs from those shown in FIG. 1 owing to the fact that the coupling means 11 comprise a locking bolt 28, which can be passed through the borehole 20, which passes through the prosthesis 1 and the counterpart 6 coaxially with the central axis 4. The locking bolt 28, with its head 29, can be brought into contact with the outer end 15 of the counter part 6 and has, at its tip, radially and elastically deformable cams 31, which, when the prosthesis 1 and the counterpart 6 are assembled, can be locked in an eccentric relief 30, the diameter of which is larger than the diameter of the borehole 20, so that the prosthesis 1 and the counterpart 6 are held together. For introducing the locking bolt 28 into the borehole 20, the cams 31 can be compressed perpendicularly to the central axis 4 by means of axially disposed slots 32, so that the locking bolt 28 can be passed through the borehole 20, while, in the assembled state, the cams 31 spring back elastically and latch into the eccentric relief 30 at the prosthesis 1. A hole is drilled through the locking bolt 28 coaxially with the central axis 4, so that a pin 25 can be passed through it, as a result of which a radial deflection of the cams 31 is prevented In FIG. 5, a further embodiment of the inventive prosthesis 1 with a counterpart 6 is shown. At the outer end 8 of the prosthesis 1 as well as at the outer end 15 of the counterpart 6, the processes 3 are mounted once again perpendicularly to the central axis 4 and diametrically opposite to one another, the processes 3 in this embodiment having a semicircular cross sectional surface parallel to the central axis 4. The depression 5 passes through the prosthesis 1 from the inner end 7 to the outer end 8 coaxially with the central axis 4. In the depression 5, there is an internal thread 36 with a very large pitch. Adjoining the inner end 14, the counterpart 6 once again has a peg 16, which has an external thread 33 that is complementary to the internal thread 36, so that the prosthesis 1 and the counterpart 6 can be fastened detachably to one another by means of this screwed connection. A first saw tooth-like system 34 is mounted at the counterpart 6 between the peg 16 and the processes 3 and can be brought into engagement with a complementary second tooth system 35 at the inner end 7 of the prosthesis 1 during the assembly of the prosthesis 1 and the counterpart 6 so that, due to the asymmetric configuration of the saw tooth systems 34, 35, a safeguard is provided against the unintentional detachment of the prosthesis 1 from the counterpart 6.

The invention claimed is:

1. An interspinal prosthesis for implantation between a first spinous process and a second spinal process, the prosthesis comprising:
    a first half comprising a coupling portion and a process portion, the coupling portion having a bore and configured for insertion into the interspinal space between the first spinous process and the second spinal process, the process portion being sized and configured to be placed on one side of the first and second spinous processes and being sized and configured to prevent its advancement into the interspinal space;
    a second half comprising a coupling portion and a process portion, the coupling portion configured to be received within the bore of the coupling portion of the first half, the process portion being sized and configured to be placed on the other side of the first and second spinous processes and being sized and configured to prevent advancement into the interspinal space;
    a locking mechanism for axially locking the first and second halves together after at least the coupling portion of the first half has been inserted into the interspinal space;
    wherein the coupling portion of the first and second halves are sized and configured to be elastically deformable such that the coupling portion in the area between the first and second spinous processes has an unstressed diameter and a deformed diameter, said deformed diameter being between about 10% to about 50% of the unstressed diameter; and
    wherein one of the first half and the second half includes a plurality of radially extending cams and the other of the first half and the second half includes a plurality of grooves for receiving the plurality of cams when the coupling portion of the second half is received within the bore of the coupling portion of the first half so that rotation of the first half with respect to the second half is prevented.

2. The interspinal prosthesis of claim 1, the first and second halves comprising an assembled condition and an unassembled condition, the coupling portions of the first and second halves insertable into the interspinal space in the unassembled condition, wherein engaging the coupling portion of the first half with the coupling portion of the second half configures the halves in the assembled condition.

3. The interspinal prosthesis of claim 1, wherein at least a portion of at least one of the first and second halves is made of an elastomeric material.

4. The interspinal prosthesis of claim 1, wherein at least a portion of at least one of the first and second halves further comprises a surface for enhancing bone ingrowth.

5. The interspinal prosthesis of claim 4, wherein the surface has a roughened profile.

6. The interspinal prosthesis of claim 4, wherein the surface comprises a hydroxyapatite coating.

7. The prosthesis of claim 1, wherein the coupling portion of the first half comprises a stop surface configured to axially engage the second half.

8. The prosthesis of claim 7, wherein stop surface is configured to separate the process portions of the first and second halves by an amount in the range of from about 2 mm to about 15 mm.

9. The prosthesis of claim 1, wherein the coupling portion of the first half comprises a cross-sectional dimension of from about 50 mm2 to about 300 mm2.

10. The prosthesis of claim 9, wherein the process portions of the first and second halves each have a cross sectional dimension of from about 70 mm2 to about 500 mm2.

* * * * *